United States Patent [19]

Thompson

[11] 4,446,056

[45] May 1, 1984

[54] PREPARATION OF MIXTURE OF NITROGEN AND SULFUR-NITROGEN HETEROCYCLICS AND USE IN CORROSION INHIBITING

[75] Inventor: Neil E. S. Thompson, Creve Coeur, Mo.

[73] Assignee: Petrolite Corporation, St. Louis, Mo.

[21] Appl. No.: 101,953

[22] Filed: Dec. 10, 1979

[51] Int. Cl.$^3$ .................. C23F 11/04; C23F 11/16
[52] U.S. Cl. .................. 252/391; 252/8.55 C; 252/8.55 E; 252/150; 422/12
[58] Field of Search ........... 252/391, 8.55 E, 150; 422/12

[56] References Cited

U.S. PATENT DOCUMENTS

| | | | |
|---|---|---|---|
| 2,154,096 | 4/1939 | Loane | 252/391 X |
| 2,453,882 | 11/1948 | Viles et al. | 252/8.55 E |
| 2,542,982 | 2/1951 | Bartleson et al. | 252/391 X |
| 4,106,904 | 8/1978 | Oude Alink et al. | 252/392 X |

*Primary Examiner*—Richard D. Lovering
*Attorney, Agent, or Firm*—Sidney B. Ring; Hyman F. Glass; Leon J. Bercovitz

[57] ABSTRACT

A process of preparing sulfur-containing compositions which comprises reacting hexahydrotriazines, or the precursors thereof, with sulfur or sulfur-containing compounds. The products of the reaction are useful as corrosion inhibitors. Additionally, ketones or the reaction products of ketones and ammonia are reacted with sulfur or sulfur-containing compounds to yield corrosion inhibitors.

15 Claims, No Drawings

PREPARATION OF MIXTURE OF NITROGEN AND SULFUR-NITROGEN HETEROCYCLICS AND USE IN CORROSION INHIBITING

There is described in U.S. Pat. No. 4,106,904 a novel process of preparing alkylpyridines and N-substituted alkyldihydropyridines from aldehydes with ammonia.

The process of said patent involves the formation of hexahydrotriazines from aldehydes and ammonia and, under the influence of a catalyst, thermally reacting the hexahydrotriazines to yield mixtures of alkylpyridines and N-substituted alkyldihydropyridines. The mixture obtained in this way may be further reacted to form (a) mixtures of alkylpyridines and N-substituted alkylpyridinium salts, (b) mixtures of alkylpyridines and amines or (c) alkylpyridines.

Aldehydes,

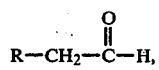

and ammonia react to form hexahydrotriazines according to the equation:

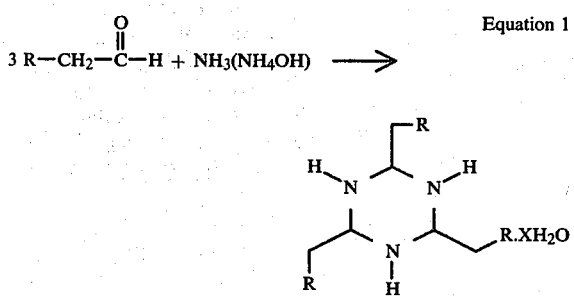
Equation 1

When reacted in the presence of a Lewis acid catalyst, hexahydrotriazines yield a mixture of alkylpyridines and N-substituted alkyldihydropyridines. The initial product is an unstable dihydropyridine formed according to the following equation:

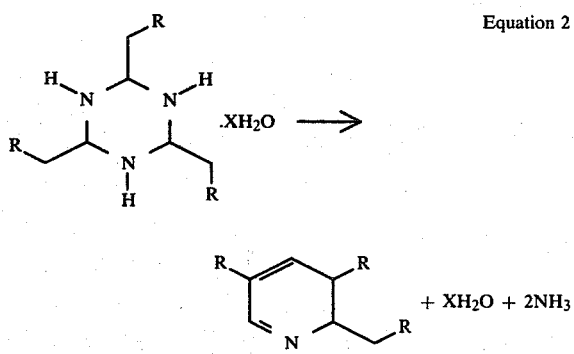
Equation 2

This dihydropyridine then reacts with the starting material in a disproportionation reaction to yield an alkylpyridine and an amine according to the equation:

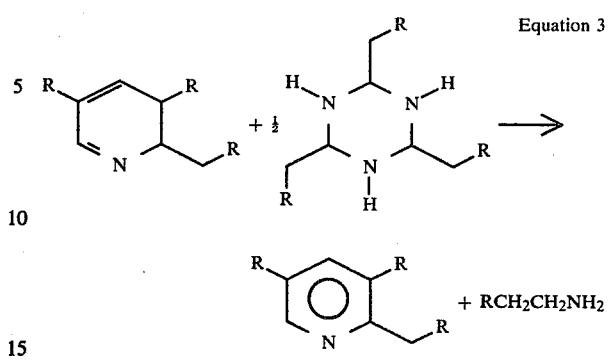
Equation 3

The amine then reacts with the starting hexahydrotriazine to yield an N-substituted alkyldihydropyridine which under reaction conditions is stable according to the equation:

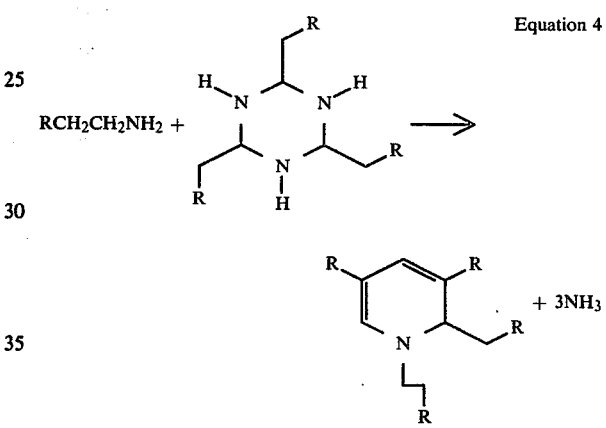
Equation 4

The overall reaction equation may be written as follows:

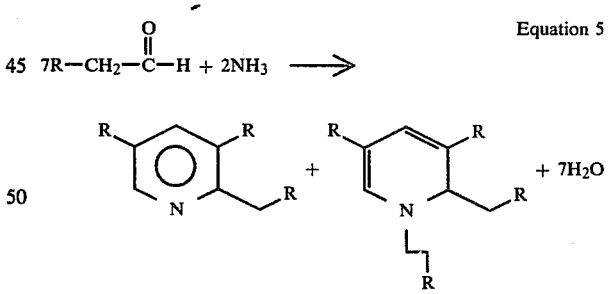
Equation 5

This reaction product of 4,106,904 may be further modified by a. reacting the final reaction product, in the presence of an acid, with air to yield an alkylpyridine and an N-substituted alkylpyridinium salt according to the equation:

Equation 6

-continued

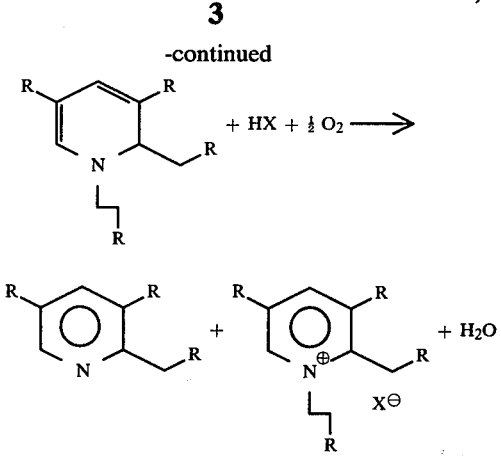

where HX is an acid, including organic and inorganic acids, for example, sulfuric acids, halogen acids such as hydrochloric, hydrobromic, and organic acids such as acetic, propionic, benzoic, sulfonic acids, etc.

b. thermally reacting the alkylpyridine and alkylpyridinium salt to yield an alkylpyridine according to the equation:

Equation 7

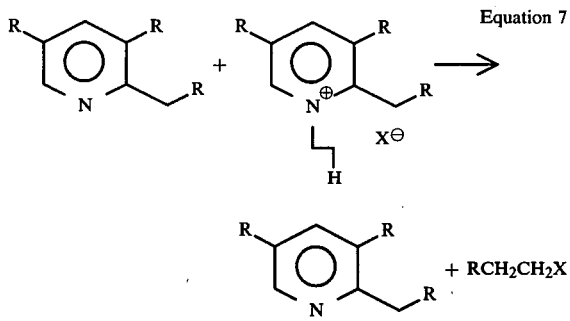

and c. reacting the mixture of alkylpyridine and N-substituted alkyldihydropyridine to yield a mixture of alkylpyridine and the Diels-Alder dimer of the dihydropyridine according to the equation:

Equation 8

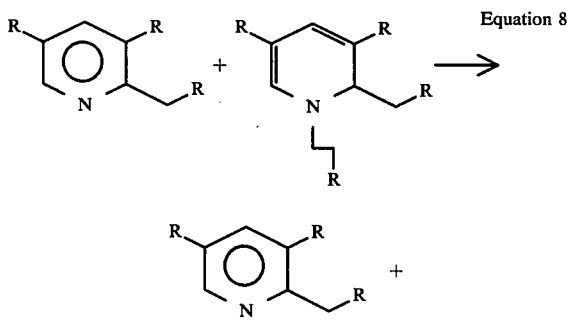

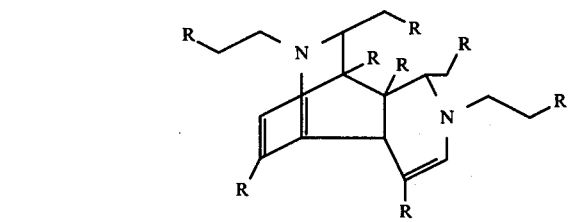

R in the above equations corresponds to the R of the aldehyde described below as

RCH$_2$CH.

The reaction of U.S. Pat. No. 4,106,904 can be carried out in two different ways. In the first method a mixture of the hexahydrotriazine and aldehyde are pre-reacted in the presence of a weak Lewis acid catalyst with the removal of the water produced. The disadvantage of this process is that side reactions such as aldol condensation of the aldehyde can take place.

The second method of U.S. Pat. No. 4,106,904 comprises heating the hexahydrotriazine. The ammonia gas evolved in this reaction can be collected in a scrubber system. It is advantageous to collect the ammonia gas in a scrubber system containing the aldehyde. In this way the hexahydrotriazine can be produced from the ammonia produced.

I have now discovered a novel process of preparing new and highly effective corrosion inhibitors by reacting aldehydes and ketones with ammonia in the presence of sulfur and/or some sulfur containing compounds. I have now discovered that the addition of sulfur or sulfur-containing compounds to the above mentioned processes results in a dramatic and significant increase in the effectiveness of these products when employed as corrosion inhibitors. The reaction product from these reactions now contain besides the alkylpyridines and N-substituted dihydropyridines and other products described in U.S. Pat. No. 4,106,904 various substituted thiazolines and thiazoles. This combined mixture of nitrogen and sulfur-containing heterocyclic system effects new and highly effective corrosion inhibition systems.

The sulfur or sulfur containing moiety can be added at various stages during the reaction. The sulfur content can vary between about 1-20% or more by weight, such as from about 1-15%, for example from 1-10%, but preferably from about 1-8%, based on the weight of the carbonyl compound charged. The most effective level of sulfur being 1-5% by weight.

Except for the presence of S, the reaction is carried out similarly to the procedure of U.S. Pat. No. 4,106,904.

Any suitable aldehyde can be employed, i.e., any aldehyde having a

—CH$_2$CH group except acetaldehyde. This includes aldehydes of the formula

RCH$_2$CH where R is alkyl, aryl, cycloalkyl, alkaryl, aralkyl, heterocyclic, etc. R is preferably alkyl, for example having from 1 to 30 or more carbons such as from 1 to 18 carbons, but preferably from about 1 to 12 carbons. The R in the above equation corresponds to the R of the aldehyde.

These include propionaldehyde, butyraldehyde, heptaldehyde, etc., as well as substituted aldehydes, such as aldol, etc.

Any suitable ketone can be employed. These include alkyl, aryl, cycloalkyl, alkaryl, aralkyl, etc. ketones. These may be ideally presented as follows:

where R and R', which may be the same or different, are alkyl, aryl, cycloalkyl, alkaryl, aralkyl, etc. In addition, the R groups may be joined to form a cyclic ketone ideally presented as

where the bracket represents a cyclic structure. These include cycloalkyl groups such as cyclohexanone, substituted cyclohexanones, etc.

Any suitable reaction temperature may be employed. In practice, the hydrotriazines are generally prepared at relatively low temperatures such as from about 20° to about 70° C., but preferably at 10°–35° C.

The alkyl pyridines and N-alkyldihydropyridines are generally prepared at higher temperatures, such as from about 80° to 300° C., but preferably from about 110° to 180° C.

The reaction time should be sufficient to prepare the desired product such as from about 0.5 to 24 hours or more. In practice, these reactions are generally carried out for about 2 to 4 hours.

The catalyst employed is of the Lewis acid type. Typical catalysts include salts, such as inorganic and organic acids, for example ammonia or amine salts of the general formula

where (N) is ammonia or amine and X is an anion, for example a halide (Cl, Br, F, I) or carboxylic acid, sulfuric acid. Illustrative examples include NH$_4$ Acetate
NH$_4$Cl
NH$_4$Br
NH$_4$I
NH$_4$benzenesulfonate, etc.

Zinc halide such as zinc chloride, silica, etc. Other catalysts include AlCl$_3$, FeCl$_3$ PbO, Al$_2$O$_3$, etc.

The following examples are presented for purposes of illustration and not of limitation.

EXAMPLE 1

To a suitable reactor is charged 300 cc of aqueous ammonia (NH$_4$OH~58%). Butyraldehyde (200 grams) is added at a rate such that the reaction mixture is maintained at 35°–45° C. Addition time is about 45 min. Stirring is continued for an additional 90 minutes and then the mixture is allowed to settle and separate into two phases. The upper organic phase was identified as 2,4,6-tripropyl 1,3,5-hexahydrotriazine, containing 1 mole of water. Anal. calculated for C$_{12}$H$_{27}$N$_3$. H$_2$O: N, 18.2; Found 17.9.

The organic phase (200 grams) was charged to a 500 ml reactor equipped with stirrer, thermometer and off-gas condenser attached to a Dean Stark trap. Ammonium nitrate, 2 grams was added and the mixture heated gradually to 180° C. over a 4 hour period. During this period copious evolution of ammonia gas took place; low boiling products, mainly water, were removed during the reaction. The product (160 gm) was a clear amber liquid. The product was separated by preprative gas chromatography into two major components. These were identified as 2-propyl 3,5-diethyl pyridine and 1-butyl,2-propyl, 3,5-diethyl 1,2-dihydropyridine.

EXAMPLE 2

To 100 grams of 2,4,6-tripropyl 1,3,5-hexahydrotriazine prepared as described in example 1, was added 1.5 grams ammonium nitrate and 1.0 gram sulfur. The mixture was heated as described in example 1 and the resulting product was a clear amber stench liquid. Analysis showed incorporation of 90% of the sulfur added.

Using the reactants and procedure of Example 2 except for the following % of sulfur and/or sulfur-containing reactant, the following sulfur-containing compositions were prepared. The results are summarized in Table 1.

TABLE 1

| Example No. | Sulfur Compound | Wgt. of Sulfur-containing Reactant | % Sulfur of wgt. of Reactants |
|---|---|---|---|
| 3 | sulfur | 5 | 5 |
| 4 | sulfur | 10 | 10 |
| 5 | sulfur | 20 | 20 |
| 6 | Thiourea | 11.6 | 5 |
| 7 | Thiourea | 23.2 | 10 |
| 8 | Thioacetamide | 11.6 | 5 |
| 9 | P$_2$S$_5$ | 7.0 | 5 |

EXAMPLE 10

To a cooled aqueous 28% ammonia solution (300 cc) and sulfur (10 grams) was added 200 grams butyraldehyde at such a rate that a temperature of ≦35° C. was maintained. The mixture was stirred for 24 hours and the resulting layers were separated, in an upper organic phase and lower aqueous phase. The organic phase was charged to a reactor equipped with stirrer, thermometer, and an off-gas condenser attached to a Dean Stark trap. Ammonium nitrate, 2 grams, was added and the mixture heated gradually to 180° C. over a period of 4 hours. During this period copious evolution of ammonia gas took place; low boiling products, mainly water, were removed during the reaction. The resulting product was a clear amber stench liquid. Analysis indicated ≧90% of sulfur charged present in the product.

As described in example 10, the following sulfur containing compositions were prepared. The details are summarized in Table 2.

TABLE 2

| Example No. | Sulfur Compound | Wt. Sulfur Compound | % Sulfur of Wgt. of Reactants |
|---|---|---|---|
| 11 | sulfur | 1.0 g | 0.5 |
| 12 | sulfur | 5.0 g | 2.5 |
| 13 | sulfur | 20.0 g | 10.0 |
| 14 | Thiourea | 5.0 g | 1.0 |
| 15 | P$_2$S$_5$ | 5.0 g | 1.8 |

EXAMPLE 16

Place in a pressure reactor, a mixture of 200 grams cyclohexanone and 10 grams ammonium nitrate. Add with stirring ammonia gas and maintain a pressure of 30-40 psi while keeping the reaction temperature between 50°-60° C. Continue stirring for 10-24 hours or until the reaction shows no sign of taking up more ammonia. When the reaction is over the stirrer is turned off and the mass upon settling separates into two layers. The lower viscous organic which is identified as 2,2,4,4-dipentamethylene 5,6-tetramethylene 2,2,4,5-tetrahydropyrimidine is charged to a 500 ml reactor equipped with stirrer, thermometer and an off-gas condenser attached to a Dean Stark trap. Carefully add 4 grams nitric acid or 10 grams ammonium nitrate and heat the mixture gradually to 190°-200° C. for 5-6 hours while removing any water or low boiling distillate. Evolution of ammonia gas commences at about 110°-120° C. and is very strong at 150° C. The progress and completion of the reaction can be followed by the decrease in the off gas evolution and by the change in the infrared spectral characteristics, the peak at 6.02μ, —C≡N, disappears and a strong new peak at 6.4μ (pyridine) appears. The final product (175 grams) is a dark very viscous liquid and is identified as 9-pentyl 1,2,3,4,5,6,7,8-octahydrophenanthridine).

EXAMPLE 17

To 100 grams of the intermediate pyrimidine prepared as described in example 16 was added 10 grams sulfur and 5 grams ammonium nitrate and the mixture heated gradually to 190°-200° C. for 6 hours. The resulting product was a dark very viscous stench liquid. Analysis showed ≧85% of sulfur charged present in the final product.

EXAMPLE 18

Same as example 17 except 5.0 grams sulfur was added.

EXAMPLE 19

Same as example 17 except 1.0 gram sulfur was added.

EXAMPLE 20

Place in a pressure reactor a mixture of 200 grams cyclohexanone, 10 grams sulfur and 10 grams ammonium nitrate. Add with stirring ammonia gas and maintain a pressure of 30-40 psi while keeping the reaction temperature between 50°-60° C. This reaction is exothermic and some cooling might be required. Continue stirring for 10-20 hours. When the reaction is over, the stirrer is turned off and the mass upon settling separates into two layers. The lower organic layer (205 grams) is drawn off and charged to a 500 ml reactor equipped with stirrer, thermometer and a Dean Stark trap attached to a reflux condenser. Carefully add 4 grams nitric acid or 10 grams ammonium nitrate and heat the mixture gradually to 190°-200° C. for 6 hours. The resulting product is a dark viscous stench liquid. Gas chromatography shows the product to consist mainly of two components, phenathridine and 2,2-pentamethylene 4,5-tetramethylene 3-thiazoline. Analysis showed ≧85% of sulfur charged present in the final product.

EXAMPLE 21

Same as example 20, except 20 grams sulfur was added. This product was a semi-solid.

EXAMPLE 22

Same as example 20, except 5 gms sulfur was added.

EXAMPLE 23

Same as example 20, except 2 grams sulfur was added.

TABLE 3

| Example No. | Sulfur Compound | Wgt. Sulfur Compound | % Sulfur of Wgt. of Reactants |
|---|---|---|---|
| 16 | — | — | — |
| 17 | Sulfur | 10 | 10 |
| 18 | " | 5 | 5 |
| 19 | " | 1 | 1 |
| 20 | " | 10 | 5 |
| 21 | " | 20 | 10 |
| 22 | " | 5 | 2.5 |
| 23 | " | 2 | 1.0 |

The sulfur containing heterocyclic products are primarily thiazoles and thiazolines characterized by the presence of the following moieties:

(1) Thiazole

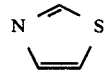

(2) Thiazoline

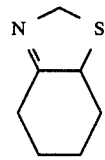

and substituted derivatives thereof, for example

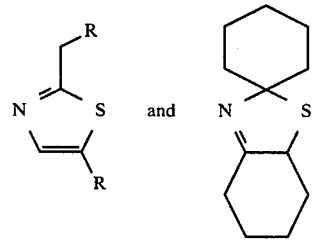

where R is the R moiety of the aldehyde or ketone reacted.

The following is an outline of the reactions occurring in the above examples.

EXAMPLE 1

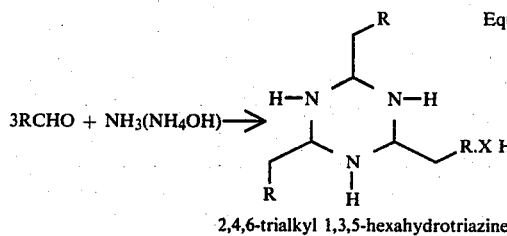

Equation 1

2,4,6-trialkyl 1,3,5-hexahydrotriazine

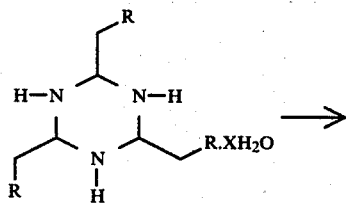

Eq. 2

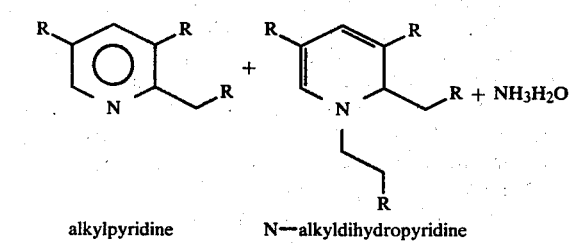

alkylpyridine    N—alkyldihydropyridine

EXAMPLES 2-5

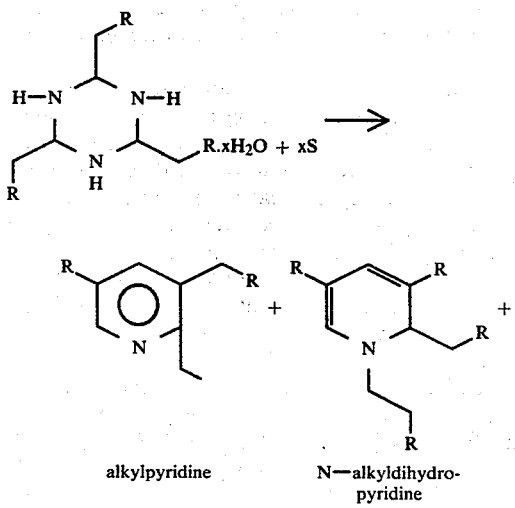

alkylpyridine    N—alkyldihydro-
pyridine

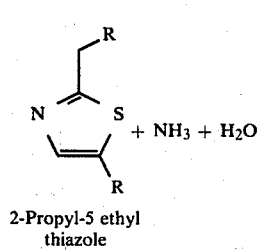

2-Propyl-5 ethyl
thiazole

EXAMPLES 10-13

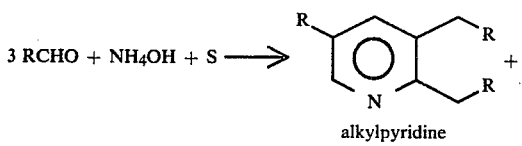

alkylpyridine

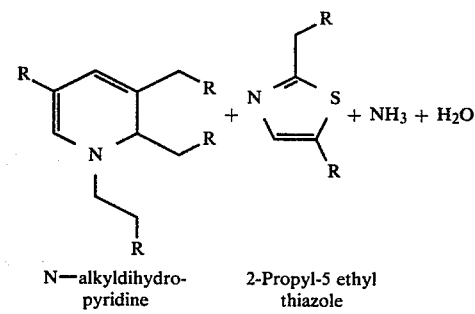

N—alkyldihydro-
pyridine    2-Propyl-5 ethyl
thiazole

EXAMPLE 16

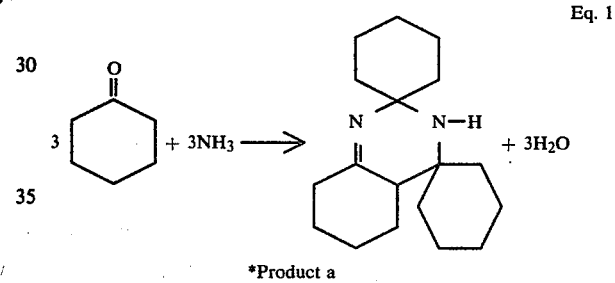

Eq. 1

*Product a

*2,2,4,4-dipentamethylene 5,6-tetramethylene
2,2,4,4-tetrahydropyrimidine

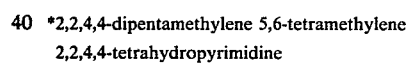

Eq. 2

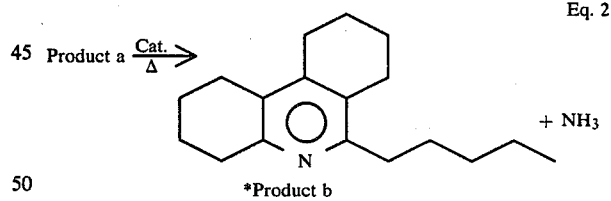

*Product b

*9-pentyl 1,2,3,4,5,6,7,8-octahydrophenanthridine

EXAMPLES 17-19

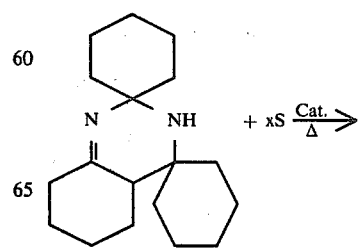

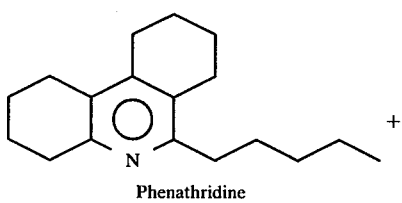
Phenathridine

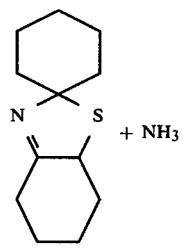
2,2-pentamethylene 4,5-tetramethylene 3-thiazoline

EXAMPLES 20-23

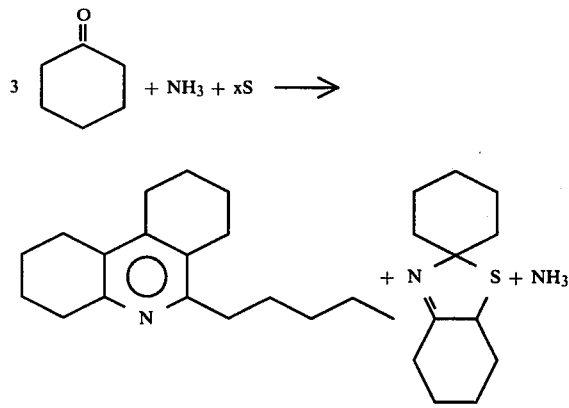

Note that no equations are given for the reaction with other than elemental sulfur such as in the following examples:
6—thiourea
7—thiourea
8—Thioacetamide
9—P$_2$S$_5$
14—Thiourea
15—P$_2$S$_5$ Although the products of these reactions with sulfur-containing compounds are effective as corrosion inhibitors, the exact structure of these products has not been determined.

USE AS CORROSION INHIBITORS

This phase of this invention relates to the use of these compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require a protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is on contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$ air or oxygen, etc.

The method of carrying out this process is relatively simple in principle. The corrosion preventive compound is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, air or oxygen, organic acids and the like. For the protection of such wells, the compound, either undiluted or dissolved in a suitable solvent, is fed down the annulus of the well between the vice or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below the casing. In such wells the compound may be introduced into the tubing through a pressure equalizing vessel, after stopping the flow of fluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the specific compound being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described compounds appears to be maintained for an appreciable time after treatment ceases, but eventually is lost unless another application is made.

For example, for the protection of gas wells and gas-condensate wells, the amount of corrosion inhibitor used might range between about ¼ to 3 lbs. per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compounds are particularly effective in the prevention of corrosion in systems containing a corrosive aqueous medium, and most particularly in system containing brines.

These compounds can also be used in the prevention of corrosion in the secondary recovery of petroleum by water flooding and in the disposal of waste water and brine from oil and gas wells. Still more particularly, they can be used in a process of preventing corrosion in water flodding and in the disposal of waste water and brine from oil and gas wells which is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which is can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have discovered a method of preventing corrosion in systems containing a corrosive aqueous media, and most particularly in systems containing brines, which is characterized by employing the compounds described herein. For example, I have discovered an improved process of protecting from corrosion metallic equipment employed in secondary oil recovery by water flooding such an injection wells, transmission lines, filters, meters, storage tanks, and other metallic implements employed therein and particularly those containing iron, steel, and ferrous alloys, such process being characterized by employing in water flood operation an aqueous solution of the compositions of this invention.

The invention, then, is particularly concerned with preventing corrosion in a water flooding process characterized by the flooding medium, containing an aqueous or an oil field brine solution of these reagents.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compounds of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from being plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular compound, the particular system, etc. Concentration of at least about ¼ p.p.m., such as about ¼ to 7,500 p.p.m., for example about 1 to 5,000 p.p.m., advantageously about 10 to 1,000 p.p.m., but preferably about 15–250 p.p.m., may be employed. Larger amounts can also be employed such as 1.5–5.0% although there is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition. Since these compounds are themselves inexpensive and are used in low concentrations, they enhance the success of a flood operation by lowering the cost thereof.

USE IN ACID SYSTEMS

The compounds of this invention can be employed as corrosion inhibitors for acid systems, for example as illustrated by the pickling of ferrous metals, the treatment of calcareous earth formations, etc., as described in the following sections.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc. for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the compounds of this invention, for example at least about 5 p.p.m., such as from about 100 to 50,000 p.p.m., about 500 to 30,000, but preferably from about 3,000 to 10,000 p.p.m.

Ferrous metal articles are pickled by contacting the surface (usually by immersions in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

CORROSION TESTS

The compositions of this invention were evaluated as corrosion inhibitors in HCl pickle acid systems and in "sweet" $CO_2$/brine corroding environment. The test procedure and results are discussed below.

HCl Pickle Acid Inhibitors

The HCl pickle acid solution was prepared as follows: to 500 ml of tap water was added 135 ml of reagent grade (37%) HCl. And to this 240 g $FeCl_2.4H_2O$ and dilute to 1000 ml with tap water. This gives a solution of about 5% HCl and 7% Fe.

Test Procedure

Heat oil bath to 160° F. Place 200 ml of HCl pickle acid in a 300 ml beaker and place beaker in oil bath. Leave acid in oil bath for one (1) hour for temperature to stabilize. Add inhibitor to be tested at 1000 ppm based on active ingredient. Clean the corrosion coupons by immersing briefly (5–10 seconds) in 15% HCl, then in hot water, then in acetone and air dry. Weigh coupons to the nearest 0.0001 gm. The coupons used are 1020 mild steel, ⅞×3¼×1/6 inch. Place the weighed coupons in the test beakers at 30 second intervals and allow to corrode for one (1) hour. Remove coupons at 30 second intervals in original sequence. Immediately on removal from the test beaker wash coupon in hot water to remove the acid, then in warm acetone and air dry. Reweigh dried coupons to the nearest 0.0001 gram. The percent protection (inhibition) is calculated as follows:

$$\% \text{ Protection (Inhibition)} = \frac{\text{Blank wt. loss} - \text{Test wt. loss}}{\text{Blank wt. loss}} \times 100$$

For accuracy and precision, run all tests in triplicate and run a blank each time.

The results are presented in Table 3 where the inhibitor concentration in each example is 1000 ppm.

TABLE 3

| Product of Example | Percent Protection |
|---|---|
| 1 (no sulfur) | 68 |
| 2 | 85 |
| 3 | 88 |
| 4 | 88 |

TABLE 3-continued

| Product of Example | Percent Protection |
|---|---|
| 5 | 80 |
| 6 | 86 |
| 8 | 85 |
| 9 | 84 |
| 10 | 88 |
| 11 | 80 |
| 14 | 82 |
| 16 (no sulfur) | 85 |
| 17 | 88 |
| 18 | 95 |
| 19 | 93 |
| 20 | 96 |
| 21 | 85 |
| 22 | 93 |
| 23 | 92 |

TEST FOR "SWEET" CORROSIVE SYSTEMS

$CO_2$ Brine Sparge Test

The $CO_2$/brine sparge test is a reliable quick test to screen compounds as potential corrosion inhibitors in "sweet" corrosive systems. A laboratory brine solution is sparged with stirring with 99.9% grade $CO_2$ for about one hour before immersing the cleaned and weighed corrosion coupons. A M-1010 PAIR meter was used to monitor the corrosion rate of each test cell. After one to two hours the corrosion rate reached a "steady state," but a precorrosion period of 3.5 hours was used for consistency before the test inhibitor was added. The precorroding period in the inhibited brine solution is very important. This provides a precorroded test surface thereby minimizing surface preparation variations and also provides at least a minimal corrosion product layer without inhibitor in it against which the test inhibitor must work. This step is important, because in the equipment, the inhibitor is only rarely used from day one and then when it is used it is used on rusted steel and not freshly sand-blasted surfaces.

The inhibitors were injected below the brine surface at 50 ppm based on the active component. The 48 hour test period was monitored with a M-1010 PAIR meter as a "back-up," but the corrosion rates and percent protection were determined by weight loss measurements.

Examples of sweet corrosive systems include carbon dioxide-containing gas systems such as sweet gas lines, sweet gas wells, etc.

The test results are summarized in Table 4.

TABLE 4

| Product of Example | Percent Protection |
|---|---|
| 1 (no sulfur) | 40 |
| 2 | 78 |
| 3 | 82 |
| 4 | 78 |
| 5 | 69 |
| 6 | 77 |
| 8 | 75 |
| 9 | 72 |
| 10 | 80 |
| 11 | 70 |
| 14 | 72 |
| 16 (no sulfur) | 41 |
| 17 | 25 |
| 18 | 80 |
| 19 | 70 |
| 20 | 85 |
| 21 | 39 |
| 22 | 85 |

TABLE 4-continued

| Product of Example | Percent Protection |
|---|---|
| 23 | 78 |

The results clearly demonstrate the effectiveness of the sulfur containing compositions. The results also indicate that when the sulfur level is >10% the corrosion inhibitor properties may decrease and in some cases the inhibitor acts as a pro-corrosive agent. However this is not true for all corrosive systems.

The following is presented to illustrate that the compositions of this invention are more effective than the sulfur composition present in the compositions.

TABLE 5

| | % Protection Corrosion Tests | |
|---|---|---|
| Compound | HCl Pickle Acid Test | $CO_2$/Brine Sparge Test |
| 2,2-pentamethylene-4,5-tetramethylene thiazoline | 65 | 10 |
| 2-Propyl-5 ethyl thiazole | 62 | 0 |
| 2,2,4-Triethyl-5-methyl thiazoline | 43 | 0 |

I claim:

1. A process of preparing sulfur-containing compositions which comprises reacting hexahydrotriazines in the presence of a Lewis acid at a temperature between 80° C. and 300° C. for a period of about 0.5 to 24 hours, or the precursors thereof, with a member from the group consisting of sulfur and sulfur-containing compounds, where the precursors are aldehydes, except for acetaldehyde, reacted with ammonia.

2. The product of claim 1.

3. A process of inhibiting corrosion which comprises treating a system with the product of claim 2.

4. The process of claim 1 where the hexahydrotriazine is derived from an alkyl aldehyde.

5. The product of claim 4.

6. A process of inhibiting corrosion which comprises treating a system with the product of claim 5.

7. The process of claim 4 where the aldehyde is butyraldehyde and sulfur is utilized.

8. The product of claim 7.

9. A process of inhibiting corrosion which comprises treating a system with the product of claim 8.

10. A process of preparing sulfur-containing compositions which comprises reacting 2, 2, 4, 4-dipentamethylene 5, 6-tetramethylene 2, 2, 4, 4-tetrahydropyrimidine, or the cyclohexanone precursor thereof, with sulfur.

11. The composition product of claim 10.

12. A composition containing alkyl or cycloalkylpyridines, N-substituted alkyl or cycloalkyl dihydropyridines and a member from the group consisting of thiazoles and thiazolines.

13. A process of inhibiting corrosion which comprises treating a system with the composition of claim 12.

14. The composition of claim 12 containing alkylpyridine, N-alkyldihydropyridine and 2-propyl-5 ethyl thiazole.

15. A process of inhibiting corrosion which comprises treating a system with the composition of claim 14.

* * * * *